US010624733B2

(12) United States Patent
Gonzalez et al.

(10) Patent No.: US 10,624,733 B2
(45) Date of Patent: Apr. 21, 2020

(54) AIRWAY STENT

(71) Applicant: SPIRATION, INC., Redmond, WA (US)

(72) Inventors: Hugo Xavier Gonzalez, Woodinville, WA (US); Clinton L. Finger, Bellevue, WA (US)

(73) Assignee: Spiration, Inc., Redmond, WA (US)

( * ) Notice: Subject to any disclaimer, the term of this patent is extended or adjusted under 35 U.S.C. 154(b) by 135 days.

(21) Appl. No.: 15/552,714

(22) PCT Filed: Feb. 17, 2016

(86) PCT No.: PCT/US2016/018170
§ 371 (c)(1),
(2) Date: Aug. 22, 2017

(87) PCT Pub. No.: WO2016/153635
PCT Pub. Date: Sep. 29, 2016

(65) Prior Publication Data
US 2018/0028306 A1 Feb. 1, 2018

Related U.S. Application Data

(60) Provisional application No. 62/137,268, filed on Mar. 24, 2015.

(51) Int. Cl.
*A61F 2/04* (2013.01)
*A61F 2/82* (2013.01)
*A61F 2/848* (2013.01)

(52) U.S. Cl.
CPC .................. *A61F 2/04* (2013.01); *A61F 2/82* (2013.01); *A61F 2002/043* (2013.01);
(Continued)

(58) Field of Classification Search
CPC .................. A61F 2/04; A61F 2002/043; A61F 2002/044; A61F 2002/046
See application file for complete search history.

(56) References Cited

U.S. PATENT DOCUMENTS 3,540,431 A 11/1970 Mobin-Uddin
3,874,388 A 4/1975 King et al.
(Continued)

FOREIGN PATENT DOCUMENTS

CN 101460113 A 6/2009
CN 102123683 A 7/2011
(Continued)

OTHER PUBLICATIONS

Office Action from the Japanese Patent Office for Application No. 2017-548916 dated Aug. 28, 2018.
(Continued)

*Primary Examiner* — Seema Mathew

(57) ABSTRACT

A stent comprising: two or more stent sections; one or more rods extending between the two or more stent sections; wherein one the one or more rods is fixedly connected to a fixed anchor that is connected to a first of the two or more stent sections, and a second of the two or more of stent sections are movable connected to one of the one or more rods by a movable anchor; and wherein the stent supports an opening of an anatomical passageway.

19 Claims, 6 Drawing Sheets

(52) U.S. Cl.
CPC ... *A61F 2002/046* (2013.01); *A61F 2002/825* (2013.01); *A61F 2002/828* (2013.01); *A61F 2002/8483* (2013.01); *A61F 2230/005* (2013.01); *A61F 2230/0041* (2013.01); *A61F 2230/0058* (2013.01); *A61F 2230/0093* (2013.01); *A61F 2250/0006* (2013.01); *A61F 2250/0007* (2013.01); *A61F 2250/0008* (2013.01)

(56) References Cited

U.S. PATENT DOCUMENTS

| | | | |
|---|---|---|---|
| 4,619,246 A | 10/1986 | Molgaard-Nielsen et al. | |
| 4,710,192 A | 10/1987 | Liotta et al. | |
| 4,727,873 A | 3/1988 | Mobin-Uddin | |
| 4,732,152 A | 3/1988 | Wallsten et al. | |
| 4,808,183 A | 2/1989 | Panje | |
| 4,819,664 A | 4/1989 | Nazari | |
| 4,830,003 A | 5/1989 | Wolff et al. | |
| 4,852,568 A | 8/1989 | Kensey | |
| 5,061,274 A | 10/1991 | Kensey | |
| 5,382,261 A | 1/1995 | Palmaz | |
| 5,413,599 A | 5/1995 | Imachi et al. | |
| 5,484,444 A | 1/1996 | Braunschweiler et al. | |
| 5,507,754 A | 4/1996 | Green et al. | |
| 5,509,900 A | 4/1996 | Kirkman | |
| 5,797,960 A | 8/1998 | Stevens et al. | |
| 5,810,837 A | 9/1998 | Hofmann et al. | |
| 5,817,101 A | 10/1998 | Fiedler | |
| 5,851,232 A | 12/1998 | Lois | |
| 5,855,601 A | 1/1999 | Bessler et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 6,027,525 A | 2/2000 | Suh et al. | |
| 6,165,179 A | 12/2000 | Cathcart et al. | |
| 6,174,323 B1 | 1/2001 | Biggs et al. | |
| 6,258,100 B1 | 7/2001 | Alferness et al. | |
| 6,267,775 B1 | 7/2001 | Clerc et al. | |
| 6,287,290 B1 | 9/2001 | Perkins et al. | |
| 6,287,334 B1 | 9/2001 | Moll et al. | |
| 6,293,951 B1 | 9/2001 | Alferness et al. | |
| 6,328,689 B1 | 12/2001 | Gonzalez et al. | |
| 6,398,775 B1 | 6/2002 | Perkins et al. | |
| 6,447,530 B1 | 9/2002 | Ostrovsky | |
| 6,488,673 B1 | 12/2002 | Laufer | |
| 6,527,761 B1 | 3/2003 | Soltesz et al. | |
| 6,544,291 B2 | 4/2003 | Taylor | |
| 6,558,429 B2 | 5/2003 | Taylor | |
| 6,585,639 B1 | 7/2003 | Kotmel et al. | |
| 6,592,594 B2 | 7/2003 | Rimbaugh et al. | |
| 6,629,951 B2 | 10/2003 | Laufer et al. | |
| 6,679,264 B1 | 1/2004 | Deem et al. | |
| 6,694,979 B2 | 2/2004 | Deem et al. | |
| 6,904,909 B2 | 6/2005 | Andreas et al. | |
| 6,941,950 B2 | 9/2005 | Wilson et al. | |
| 7,011,094 B2 | 3/2006 | Rapacki et al. | |
| 7,434,578 B2 * | 10/2008 | Dillard | A61B 17/12104 128/200.24 |
| 7,691,151 B2 | 4/2010 | Kutsko et al. | |
| 7,704,268 B2 * | 4/2010 | Chanduszko | A61B 17/0057 606/213 |
| 8,021,385 B2 | 9/2011 | Alferness | |
| 8,177,805 B2 | 5/2012 | Alferness | |
| 8,414,655 B2 | 4/2013 | Alferness et al. | |
| 8,454,708 B2 | 6/2013 | Kutsko et al. | |
| 8,603,127 B2 | 12/2013 | Alferness | |
| 8,647,392 B2 | 2/2014 | Kutsko et al. | |
| 8,998,986 B1 * | 4/2015 | Malinowski | A61F 2/18 623/10 |
| 2001/0010017 A1 | 7/2001 | Letac et al. | |
| 2001/0025132 A1 | 9/2001 | Alferness et al. | |
| 2001/0037808 A1 | 11/2001 | Deem et al. | |
| 2001/0051799 A1 | 12/2001 | Ingentio | |
| 2001/0052344 A1 | 12/2001 | Doshi | |
| 2001/0056274 A1 | 12/2001 | Perkins et al. | |
| 2002/0007831 A1 | 1/2002 | Davenport et al. | |
| 2002/0062120 A1 | 5/2002 | Perkins et al. | |
| 2002/0077593 A1 | 6/2002 | Perkins et al. | |
| 2002/0077696 A1 | 6/2002 | Zadno-Azizi et al. | |
| 2002/0087153 A1 | 7/2002 | Roschak et al. | |
| 2002/0095209 A1 | 7/2002 | Zadno-Azizi et al. | |
| 2002/0111671 A1 | 8/2002 | Stenzel | |
| 2002/0112729 A1 | 8/2002 | DeVore et al. | |
| 2002/0138135 A1 | 9/2002 | Duerig et al. | |
| 2002/0147462 A1 | 10/2002 | Mair et al. | |
| 2003/0013935 A1 | 1/2003 | Alferness et al. | |
| 2003/0018344 A1 | 1/2003 | Kaji et al. | |
| 2003/0024527 A1 | 2/2003 | Ginn | |
| 2003/0050648 A1 | 3/2003 | Alferness et al. | |
| 2003/0051733 A1 | 3/2003 | Kotmel et al. | |
| 2003/0055331 A1 | 3/2003 | Kotmel et al. | |
| 2003/0070682 A1 | 4/2003 | Wilson et al. | |
| 2003/0083671 A1 | 5/2003 | Rimbaugh et al. | |
| 2003/0127090 A1 | 7/2003 | Gifford et al. | |
| 2003/0154988 A1 | 8/2003 | DeVore et al. | |
| 2003/0158515 A1 | 8/2003 | Gonzalez et al. | |
| 2003/0167065 A1 | 9/2003 | Kumar | |
| 2003/0183235 A1 | 10/2003 | Rimbaugh et al. | |
| 2003/0212412 A1 | 11/2003 | Dillard et al. | |
| 2003/0216769 A1 | 11/2003 | Dillard et al. | |
| 2003/0228344 A1 | 12/2003 | Fields et al. | |
| 2004/0039250 A1 | 2/2004 | Tholfsen et al. | |
| 2004/0039443 A1 * | 2/2004 | Solem | A61F 2/2451 623/2.37 |
| 2004/0060563 A1 | 4/2004 | Rapacki et al. | |
| 2004/0167636 A1 | 8/2004 | Dillard et al. | |
| 2004/0206349 A1 | 10/2004 | Alferness et al. | |
| 2004/0210248 A1 | 10/2004 | Gordon et al. | |
| 2004/0210306 A1 | 10/2004 | Quijano et al. | |
| 2004/0211412 A1 | 10/2004 | Alferness et al. | |
| 2004/0243140 A1 | 12/2004 | Alferness et al. | |
| 2005/0033310 A1 | 2/2005 | Alferness et al. | |
| 2005/0033344 A1 | 2/2005 | Dillard et al. | |
| 2006/0009800 A1 * | 1/2006 | Christianson | A61B 17/0057 606/213 |
| 2006/0030932 A1 | 2/2006 | Kantor et al. | |
| 2006/0206147 A1 * | 9/2006 | DeVore | A61B 17/12022 606/213 |
| 2007/0123978 A1 | 5/2007 | Cox | |
| 2007/0232992 A1 | 10/2007 | Kutsko et al. | |
| 2007/0244517 A1 * | 10/2007 | Callaghan | A61B 17/0057 606/213 |
| 2007/0265658 A1 * | 11/2007 | Nelson | A61B 17/00234 606/213 |
| 2008/0015627 A1 * | 1/2008 | DeVore | A61B 17/12022 606/192 |
| 2008/0051911 A1 * | 2/2008 | Rucker | A61F 2/04 623/23.7 |
| 2008/0086168 A1 * | 4/2008 | Cahill | A61B 17/0057 606/213 |
| 2008/0086214 A1 * | 4/2008 | Hardin | A61F 2/04 623/23.7 |
| 2008/0119866 A1 * | 5/2008 | Alferness | A61B 17/12022 606/108 |
| 2010/0049307 A1 | 2/2010 | Ren | |
| 2011/0184439 A1 * | 7/2011 | Anderson | A61B 17/0057 606/151 |
| 2012/0172927 A1 * | 7/2012 | Campbell | A61B 17/0057 606/213 |
| 2012/0253471 A1 * | 10/2012 | Tully | A61F 2/04 623/23.65 |
| 2013/0345737 A1 | 12/2013 | Alferness et al. | |
| 2014/0330308 A1 | 11/2014 | Hart et al. | |
| 2014/0330309 A1 | 11/2014 | Gonzalez et al. | |
| 2014/0364935 A1 | 12/2014 | Eli et al. | |
| 2016/0128824 A1 * | 5/2016 | Nomura | A61F 2/94 623/23.7 |
| 2017/0172722 A1 * | 6/2017 | Dillard | A61B 1/018 |
| 2017/0281330 A1 * | 10/2017 | Liljegren | A61F 2/04 |
| 2018/0161142 A1 * | 6/2018 | Finger | A61B 17/12036 |

(56) References Cited

U.S. PATENT DOCUMENTS

2019/0059906 A1\* 2/2019 Liljegren ......... A61B 17/12036
2019/0307458 A1\* 10/2019 Mathis ................... A61B 1/267

FOREIGN PATENT DOCUMENTS

CN 103209649 A 7/2013
JP 2009-532098 A 9/2009

OTHER PUBLICATIONS

International Search Report and Written Opinion for Application No. PCT/US2016/018170 dated May 27, 2016.
How Does it Work? Redirecting Airflow, Emprove Clinical Trial. Accessed on Mar. 12, 2015 at <http://www.emphysematrial.com/ibv-valve-procedure>.
Venuta et al. Airway Stenting, Patient Selection. CTSNet, published on Aug. 21, 2008, accessed on Mar. 18, 2015 at <http://www.ctsnet.org/sections/clinicalresources/thoracic/expert_tech-1>.
Chinese Office Action from Application No. CN 201680015955.1 dated Jun. 3, 2019.

\* cited by examiner

AIRWAY STENT

FIELD

The present teachings generally relate to a mechanical airway stent and more specifically a mechanical airway stent that can open lower airway passages.

BACKGROUND

The present teachings are predicated upon providing a stent including two or more stent sections that assist in opening lower/distal or peripheral airway passages. Currently, mechanical stenting is primarily performed in upper/proximal airway passages such as trachea and bronchi. These stents are placed within an airway and expand so that an airway is held open and any restriction in an airway is reduced or eliminated. These stents are good at holding open upper airways and increasing flow through upper airways. Endobronchial stenting and endoscopic techniques for palliation of airway obstruction have been used to correct bronchial stenosis. Traditionally, these techniques are evaluated against surgical options when assessing a patient with an airway obstruction.

Current airway stents are relatively large and cannot fit into smaller airway passages such as a third division or a fourth division airway. Further, once these stents are located within an airway it can be challenging to remove these stents from the airway, and the further into an airway the stents are placed the more difficult they become to remove. Some of the stents are made from a mesh or metallic material that may be subjected to reactions with tissue which may result in granulation of tissue over the stent structure. Further this granulation may make retrieval of the stent more difficult. Examples of valves may be found in U.S. Pat. Nos. 7,691,151; 8,021,385; 8,177,805; 8,454,708; 8,603,127; and U.S. Patent Application Publication Nos. 2014/0330308 and 2013/0345737; Http://www.emphysematrial.com/by-valve-procedure, last accessed on Mar. 12, 2015, all of which are incorporated by reference herein in their entirety for all purposes.

It would be valuable to have a stent, particularly an airway stent, that can pass into smaller passageways in order to open or maintain an open passageway. What is needed is a stent that is biocompatible and does not degrade over time while located within a patient. It would be valuable to have a device that is sufficiently small that the device can fit within the lower/distal airways (e.g., a third division or smaller). What is needed is a device where all or a portion of the device inhibits tissue granulation on the device and is easily removable from an airway. It would be desirable to have a device that was longitudinally movable and rotatable to conform to the walls of a tortuous passageway.

SUMMARY

The present teachings meet one or more (if not all) of the present needs by providing an apparatus comprising: a stent comprising: two or more stent sections; one or more rods extending between the two or more stent sections; wherein one of the one or more rods is fixedly connected to a fixed anchor that is connected to a first of the two or more stent sections, and a second of the two or more of stent sections are movably connected to one of the one or more rods by a movable anchor; and wherein the stent supports an opening of an anatomical passageway.

The present teachings provide a method comprising: (a) loading the stent of the teachings herein into a cartridge; (b) inserting the cartridge into a deployment apparatus; and (c) deploying the stent into a location of interest.

The teachings herein surprisingly solve one or more of these problems by providing a stent that can pass into smaller passageways in order to open or maintain an open passageway. The teachings herein provide a stent that is biocompatible and does not degrade over time while located within a patient. The teachings herein provide a device that is sufficiently small that the device can fit within the lower/distal airways (e.g., a third division or smaller). The teachings herein provide a device where all or a portion of the device inhibits tissue granulation on the device and is easily removable from an airway. The present teachings provide a device that is longitudinally movable and rotatable to conform to the walls of a tortuous passageway.

DETAILED DESCRIPTION

Figure 1:
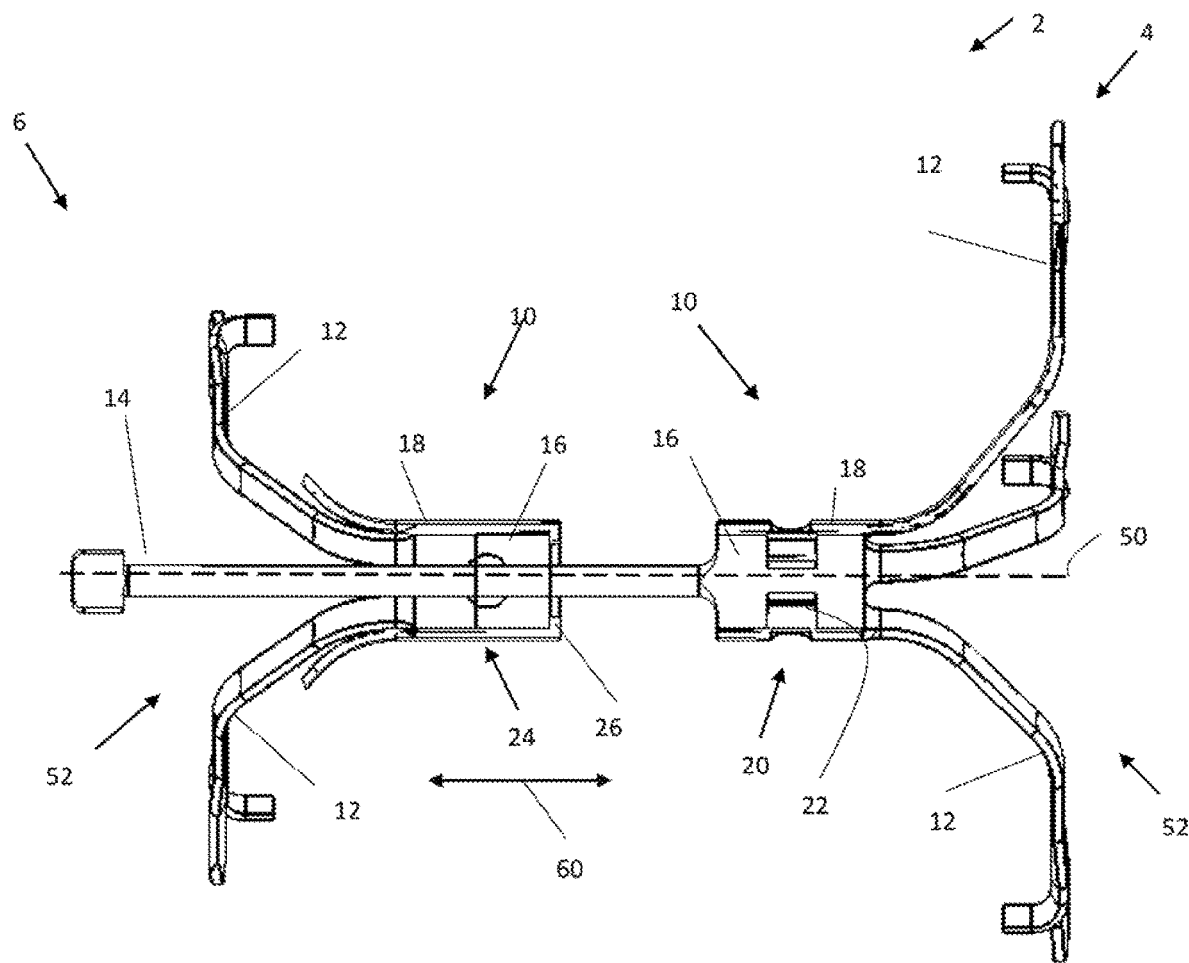
FIG. 1 illustrates an elevational view of a stent of the teachings herein.

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings claim priority to U.S. Provisional Patent No. 62/137,268, file Mar. 24, 2015. The present teachings provide an improved stent. The present teachings provide an improved airway stent. The stent functions to gradually open an airway, to maintain an openness of an airway, to remain located within a specific location in an airway, or a combination thereof. The stent may function to be removable. The stent may function to be biocompatible. The stent may extend along an axis. The stent may curve. The stent may be linear. The stent may bend in one or more locations, one or more directions, or both. The stent may bend and be rotatable. The stent may include one section. The stent may include a plurality of sections. The stent may include a distal end and a proximal end. The stent may include a longitudinal axis that extends from the distal end to the proximal end. The longitudinal axis may be linear, arcuate, include bends, or a combination thereof.

The distal end may be the lead end and/or first end placed into an airway. The distal end may include a fixed anchor. The distal end may include a terminal point, be a terminal end, or both. The distal end may include one or more blunt features so that during deployment, the distal end contacts a wall of the airway and moves the airway while the airway remains intact. If more than one stent section is present then each stent section may include a distal end. The distal end may be located opposite the proximal end. One or more of the distal ends of a stent section may be in communication with a proximal end of an adjacent stent section.

The proximal end may be the last end to be deployed. The proximal end may include one or more retraction features. The proximal end may include one or more removal features. The proximal end may include a removal rod. The removal rod may release the connection with the walls of the passage and/or airway. The removal rod may move the struts so that the struts are relaxed from the deployed state and the stent can be moved and/or removed. The proximal end may include a bulbous portion, a hook, a hole, a "J" shape, or a combination thereof that assist in forming a connection so that the stent may be removed. The proximal ends may include one or more hinge points, one or more interconnects, or both. The stent may include more than one proximal end when the stent includes more than one stent section. The stent may include two or more stent sections and even a plurality of stents sections.

The one or more stent sections may function to individually open an airway. The one or more stent sections may function to open up a length of a passage, an airway, or both. The stent sections may have a cross-sectional length (e.g., diameter) in the fully deployed state of about 5 mm or more, about 6 mm or more, about 7 mm or more, about 8 mm or more, or even about 9 mm or more. The stent sections may have a cross-sectional length in the fully deployed state of about 20 mm or less, preferably about 15 mm or less, or more preferably about 12 mm or less. Each of the one or more stent sections may be movable relative to one another. The one or more stent sections may be located along an axis. The one or more stent sections may be located end to end. The one or more stent sections may be located at an angle relative to each other (i.e., in a non-straight line). The one or more stent sections may connect to a passage or an airway. The one or more stent sections may be substantially identical. The one or more stent sections may be movable along a rod, fixed to a rod, or both. Two or more stent sections may be connected to a single rod. Each stent section may be connected to its own rod. Some stents may include multiple stent sections on one rod that are connected to an adjacent rod that includes one stent section. The one or more stent sections may include one or more struts, one or more rods, one or more stops, one or more base members, one or more fixed anchors, one or more movable anchors, or a combination thereof.

Each stent section may include two or more struts and preferably a plurality of struts. Each stent section may include two or more struts, three or more struts, four or more struts, preferably five or more struts, or even six or more struts. The struts may be evenly distributed about the rod, the base member, or both. The struts may be asymmetrically distributed about the rod, the base member or both. The struts may be movable so that more force may be applied to a predetermined location. Each stent section and the struts may exert a sufficient force on a passage or airway to open the passage or airway. Each stent section and the struts may exert a sufficient force so that a passage and/or airway is opened without damaging the passage or airway. The struts of each stent section may exert an outward force of about 0.01 Kg, or more, about 0.04 Kg, or more, about 0.06 Kg or more, or even about 0.08 Kg or more. The struts may function to expand so that the struts open an airway, a passageway, or both. The struts may function to elastically deform from a closed position (i.e., a retracted state) to an open position (i.e., deployed state). The struts may extend from being located along the longitudinal axis to extending radially outward. The one or struts may be formed into an open position and then closed until deployed where the struts elastically deform into the open position. Each strut may extend generally radially outward from a base member, a rod, or both. Each strut may form a "J" shape. Each strut may include one or more bends, two or more bends, or even three or more bends. Each strut may curve so that the strut extends radially outward from the base member. The strut as it extends outward from the base member may curve so that the angle relative to the base member becomes substantially perpendicular. Each strut in a fully relaxed state may have at least a section that forms an angle of about 90 degrees with a base member, a rod, or both. The struts may have a length. Each of the struts may have an identical length. The length of the struts from stent section to stent section may vary. For example, the stent sections at the distal end may have shorter struts then the stent sections at the proximal end so that the distal end may fit within smaller passages and/or airways. Each strut may have a total length of about 1 mm or more, about 1.5 mm or more, or even about 2 mm or more. Each strut may have a total length of about 5 mm or less, about 4 mm or less, or about 3 mm or less. Each strut may include one or more features for gripping tissue, a wall of a passage, a wall of an airway, or a combination thereof. Each strut may include one or more barbs and/or tangs that attach to tissue, a wall, or both. The struts may be made of any elastically deformable material. The struts may be made of a biocompatible material. The struts may be made of metal, plastic, polymeric material, an alloy, or a combination thereof. Preferably the struts may be made of nitinol (i.e., a nickel titanium alloy). Some struts may be directly connected to a rod and some struts may be connected to a base member. The two or more struts and preferably a plurality of struts may be connected to a base member.

Each of the base members may function to axially move along a rod. The base member may be connected to the struts. The base member and the struts may be one integral piece. The struts may be fixedly connected to the base member (e.g., welded, adhesively bonded, or both). The base member may lock to a stop, a rod, or both. The base member may move along a stop, a rod or both. The base member may be movable to allow the struts to expand radially outward. Some base members may be axially movable and some base members may be static or immoveable. The base members may be generally toroidally shaped, doughnut shaped, or both. The base members may be cylindrical. The base member may include a through hole that a rod extends through. The base member may include one or more fixed anchors, one or more movable anchors, one or more connection stops, one or more movable anchor stops, or a combination thereof. Preferably, at least one of the base members of the stent sections include a fixed anchor and at least one of the base members includes a movable anchor.

The one or more fixed anchors may function to prevent movement of one or more stent sections, one or more rods, the entire stent, or a combination thereof. The one or more anchors may function to prevent movement of the stent within a passage, an airway, or both. So that the stent remains at a desired location. The one or more fixed anchors may prevent axial movement of a stent section relative to a rod. The one or more fixed anchors may function to connect a stent section to a rod, a stop of a rod, or both. The one or more fixed anchors may be located at the distal end, the proximal end, or both ends of the stent. The one or more fixed anchors may be located in a middle section of the stent. Preferably, the one or more fixed anchors may be located at the distal end of the stent. The one or more fixed anchors may be a connection at one or more locations, may be a ring, or a combination thereof. The one or more fixed anchors may have a piece that compresses on a stop, a rod, or both. The one or more fixed anchors may have a piece that extends into a stop, a rod, or both. The one or more pieces may be one or more connection stops.

The one or more connection stops may function to prevent axial movement of a stent section, a base member, a fixed anchor, or a combination thereof along a rod. The one or more connection stops may function to form a connection so that the entire stent moves with the fixed anchor, if there is movement. The one or more connection stops may form any connection so that the rod and fixed anchor move in unison or are prevented from movement relative to the passage, an airway, or both by the struts connecting to the passage, the airway, or both. The one or more connection stops may be mechanically connected to a rod, a stop, or both (e.g., welding, crimping, friction fitting, shrinking, interlocking, or a combination thereof). The one or more connection stops may be chemically connected a stop, a rod, or both (e.g., an adhesive, heat staking, bonding, or a combination thereof). The one or more connection stops may extend into the rod, the stop, or both. The one or more connection stops may be integrally connected to the fixed anchor, be welded to the fixed anchor, adhesively connected to the fixed anchor, or a combination thereof. The one or more connection stops may be sufficiently strong so that movement of the adjacent stent sections does not move the fixed anchor and the stent remains substantially in place.

The one or more movable anchors may function to axially move one or more stent struts. The one or more movable anchors may function to allow the base member to move along a rod as the struts expand radially outward. The one or more movable anchors allow a base member to axially move along a rod without the base member being removed from the rod. The one or more movable anchors may prevent radial movement of the stent sections. The one or more movable anchors may allow for radial movement of the stent sections. The one or more movable members may be pulled or pushed along a rod by the struts deforming. The one or more movable members may be prevented from being removed from the rod, a stop, or both by one or more movable anchor stops located at one or more ends of the movable anchor, the base member, or both.

The one or more movable anchor stops may function to contact the rod, a stop, or both to limit axial movement of the strut sections in the distal direction, the proximal direction, or both. The one or more movable anchor stops may function to retain the strut section on a rod. The one or more movable anchor stops may be located at the proximal end, distal end, or both ends of the one or more of the stent sections, all of the stent sections with a movable anchor, or a combination thereof. The one or more movable anchor stops may allow for axial movement and prevent radial movement of the stent sections. The one or more movable anchor stops may restrict axial movement only, or radial moment only. The one or more movable anchor stops may allow for axial movement and radial movement. The one or more movable anchor stops may be a ring, one or more fingers, one or more tapered portions, or more restrictive features, one or more features that extend radially inward, or a combination thereof. The one or more movable anchor stops may be sufficiently large to contact a portion of a rod, a stop, or both so that the axial movement is restricted. Preferably, the movable anchor stops allow the base member to move along the rod as the struts expand and then when the movable anchor stops contact a stop on the rod, movement (e.g., axial, rotational, or both) of the stent section is prevented.

The one or more stops may function to restrict movement of the movable anchors and prevent movement of the fixed anchors. The one or more stops may be part of the rod, a discrete part connected to the rod, or both. The one or more stops may be static relative to the rod. The one or more stops may be fixedly connected to the rod so that the stop and rod are always immobile relative to each other. The one or more stops may be an increase in diameter of the rod, a change in shape of the rod, or both. The one or more stops may be fixedly connected to the rod (e.g., welded, adhesive, mechanically, or a combination thereof). The one or more stops may be friction fit, interference fit, or both on the rods. The one or more stops may have an increased cross-sectional length (e.g., diameter) relative to the rod so that one or more movable anchor stops contact the stops and restrict movement of the stent sections. The one or more stops may be made of metal, plastic, ceramic, an elastomeric material, a polymer, the same material as the rod, or a combination thereof. The one or more stops may be integrally formed on the rod or connected to the rod after formation.

The one or more rods may function to support a stent section or multiple stent sections relative to one another. The one or more rods may function to allow the stent or stent sections to be placed within a passage and/or airway, removed from a passage and/or airway, or both. The one or more rods may function to permit movement of the stent sections relative to one another. The one or more rods may include one or more curves, one or more bends, or both. Preferably, the one or more rods may be generally straight (i.e., linear). The one or more rods may be hollow, solid, or both. The one or more rods may include through holes, dimples, indentations, recesses, raised sections, non-linear sections, or a combination thereof. The one or more rods may each include a distal end and a proximal end. The distal end, the proximal end, or both may include one or more connection features, one or more removal features, one or more detachable features, or a combination thereof. The stent may include a plurality of rods that are connected together by one or more hinge points so that the stent may move through a non-linear path (e.g., a tortuous path).

The one or more hinge points may function to permit two or more of the stent sections to move relative to one another. The one or more hinge points may allow rotational movement, angular movement, or both. The one or more hinge points may allow one stent section to bend around a curve while another stent section is generally straight. The hinge points may allow for adjacent stent sections to move out of a straight longitudinal axis. For example, one stent section may move up, down, left, right, diagonally, at an angle, or a combination thereof relative to an adjacent stent section. The one or more hinge points may be located between a distal end of one stent section and a proximal end of an adjacent stent section. The one or more hinge points may allow for two or more, three or more, or even four or more degrees of freedom of one stent section relative to an adjacent stent section. The one or more hinge points may be connectable and disconnectable while the stent is located within a passage or airway. The one or more hinge points may be released by accessing a feature at a proximal end of the stent (i.e., the end closest to an exit). The one or more hinge points may have a portion that extends from a distal end to a proximal end that may be disconnected so that one of the plurality of stent sections may be removed from an airway while the rest remain within the airway. When one of the stent sections is removed, the hinge point of the next adjacent stent section may be used to remove the entire stent. The hinge points may include two or more interconnects (i.e., one interconnect extending from each stent section).

The one or more interconnects may function to form a connection between two adjacent stent sections so that a hinge point is created. The one or more interconnects may function to connect a distal end of one stent section to a proximal end of an adjacent stent section. The one or more interconnects may be a hole through a rod. The one or more interconnects may be one or more wires that are connected to and extend from a rod, a stop, a base member, or a combination thereof. The one or more interconnects may be a magnetic coupling. The one or more interconnects may be a hitch and ball. The one or more interconnects may be interlocking loops. The one or more interconnects may be interconnected rings, loops, hooks, or a combination thereof. One or both of the adjacent interconnects may be permanent, releasable, or both. One or both of the adjacent interconnects may be releasable from a proximal end, an end opposite the interconnect, or both. One or both of the interconnects may include a weakened point that is breakable by axial movement, twisting, or both. The one or more interconnects may assist the strut is moving along a longitudinal axis and to extend out of a longitudinal axis.

The strut may have a single longitudinal axis that extends from the distal end to the proximal end of the strut. The strut may have a longitudinal axis that extends substantially through the one or more rods of the strut. The strut may have sections that extend out of the longitudinal axis, at an angle relative to the longitudinal axis, rotate about the longitudinal axis, or a combination thereof. Each of the strut sections may include a longitudinal axis and the axes of each strut section may be located at an angle relative to one another. For example, the strut may extend through a tortuous section with an "S" shape and the strut sections may flex about the hinge points to fit through the tortuous section so that the axes of the sections are not aligned. One or more of the strut sections may move about the longitudinal axis of each section as the strut sections move from a retracted state to a deployed state.

The deployed state may function to open a passage, an airway, or both. The deployed state may function to extend the struts radially outward to support a stent substantially within a center of a passage and/or an airway. The deployed state may have the struts fully deployed and the movable anchors moved to a steady state location where further movement does not occur. The deployed state may have the struts extending radially outward. The fully deployed state may have the struts extending at substantially a 90 degree angle with the rod. The rods may gradually extend from the retracted state to the fully deployed state and may extend at an angle less than 90 degrees. The stent may slowly transition from a retracted state to a fully deployed state over time as the struts elastically deform back to a steady state shape. The struts may progressively open from the retracted state to the deployed state over a period of time (e.g., 6 hours or more, 12 hours or more, 24 hours or more, 1 day or more, 3 days or more, or even 1 week or more) so that a passage, airway, or both is progressively opened.

The retracted state may have the stent located within a capsule, a cartridge, or both. The retracted state may have the struts extending substantially parallel to the longitudinal axis. The retracted state may have the struts pointing away from the distal end, towards, the proximal end, or both. The retracted state may have the struts pointing in a direction so that during placement the struts do not inadvertently connect to any passages, walls, tissue, or a combination thereof. The retracted state may have the stent compacted so that the stent may travel through one or more passages, one or more air ways, or both. The retracted state may allow the stent to travel through tortuous passages, airways, or both without connecting to the walls, tissue, or both. The retracted state may allow the stent to be placed in a second division, a third division, or even a fourth division of the airway tree. The retracted state may be ended once the stent is ejected from, released from, removed from, or a combination thereof a capsule, a cartridge or both.

The stent may be loaded into a cartridge so that the struts are maintained is a folded configuration, a parallel relationship to the longitudinal axis, or both. The stent may be ejected from the cartridge so that any pressure on the struts by the cartridge is released. The endoscope, bronchoscope, or both may be pulled backwards as the stent is released so that the stent is placed within a passage, an airway, or both. The endoscope, bronchoscope, or both may be pulled back so that the stent is maintained in a desired location, a predetermined location, at a collapsed location, or a combination thereof. Once the stent is deployed the struts may function to begin elastically deforming. The struts may be configured so that the struts open a passage, an airway, or both as the struts elastically deform. The struts connected to the fixed anchor may form a connection with a passage, tissue, airway, a wall, or a combination thereof so that axial movement of the strut is substantially prevented. The struts connected to the movable anchors may form a connection with a passage, tissue, airway, a wall, or a combination thereof and axially move the movable anchor along a rod, a longitudinal axis, or both so that the struts expand as the movable anchor is moved and the stent remains substantially static.

FIG. 1 illustrates a stent 2 having a distal end 4 and a proximal end 6. The apparatus has a plurality of stent sections 10 connected to a rod 14 that extends fully and/or partially through each of the pair of stent sections 10. Each of the stent sections 10 include a base member 18 that supports a plurality of struts 12. The rod 14 includes a pair of stops 16 with one stop 16 being located in a distal end region at the distal end 4 and one stop 16 being located between the distal end 4 and the proximal end 6. Each of the stent sections 10 includes a base member 18 with a plurality of struts 12 extending therefrom and one or more anchors (20, 24). The stent sections 10 include struts 12 that are movable from a retracted state (not shown) to a deployed state 52. As shown, one base member 18 includes a fixed anchor 20 and one base member 18 includes a movable anchor 24. The fixed anchor 20 is located at a distal end 4 of the rod 14 and includes a connection stop 22 that is in communication with stop 16 so that movement of the rod 14 with respect to base member 18 is prevented at the distal end 4. The base member 18 towards the proximal end 6 includes a movable anchor 24 so that the movable anchor 24 is moved along the longitudinal axis 50 in the direction 60 towards or away from the distal end 4 and proximal end 6. The movable anchor 24 includes a movable anchor stop 26 that maintains the movable anchor 24 in communication with the stop 16 and prevents the stent section 10 from being moved.

Figure 2:
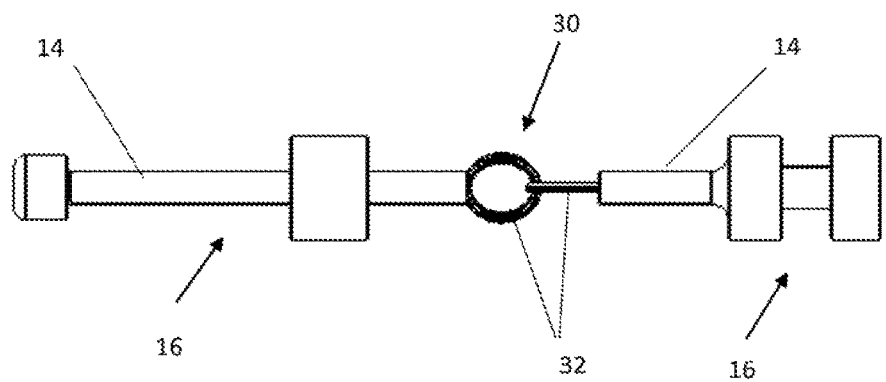
FIG. 2 illustrates an elevational view of a pair of rods connected by a hinge point.

FIG. 2 illustrates a pair of rods 14 connected together at a hinge point 30 so that the rods 14 are movable relative to each other. Each of the rods 14 include a stop 16 for connecting to stent section (not shown). The hinge point 30 as shown is an interconnect 32 that extends from opposing ends of the rods 14 so that the rods 14 are connected together and are movable relative to each other.

Figure 3:
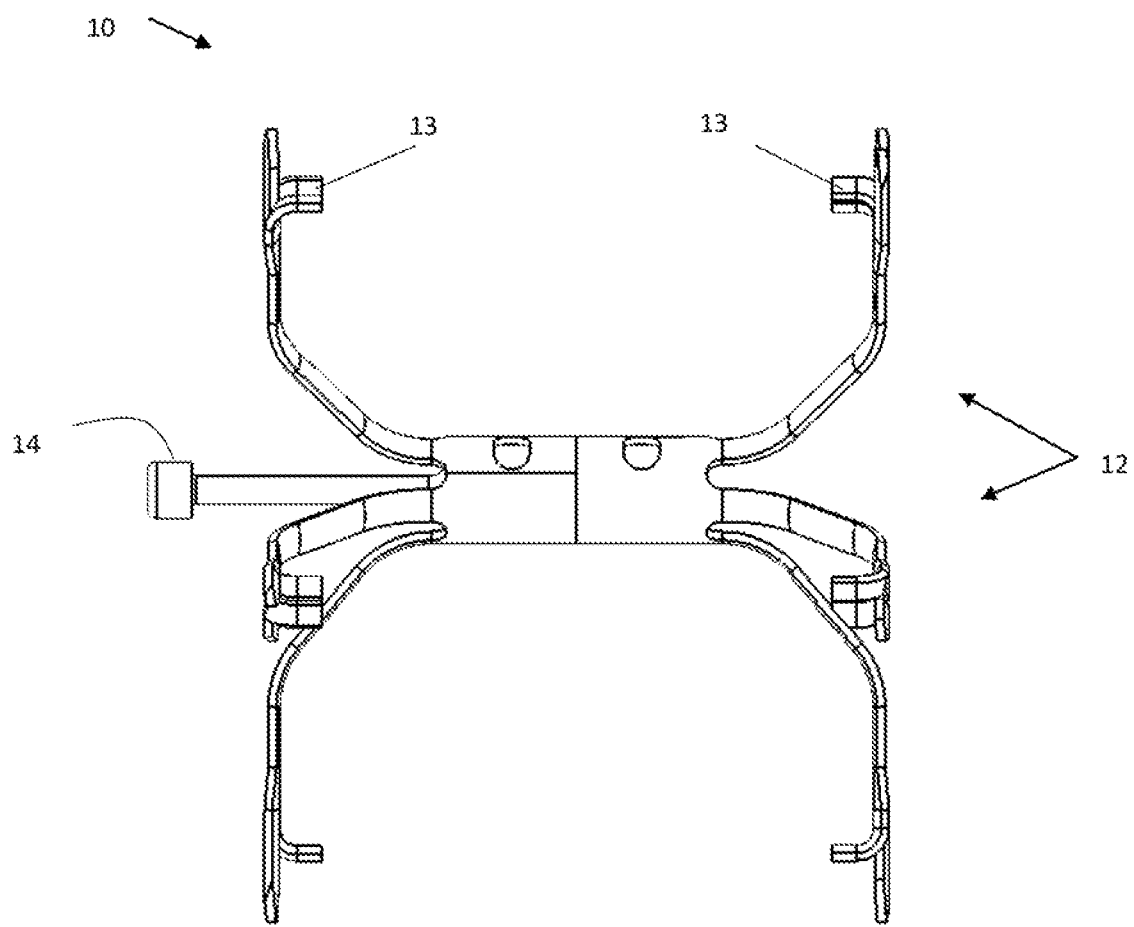
FIG. 3 illustrates a side view of a stent section.

FIG. 3 illustrates a top view of a stent section 10. The stent section 10 as shown includes struts 12 and one or more anchors 18. Each strut 12 includes a tang 13 in a distal end region of each strut 12 for connecting each strut 12 to tissue (not shown). Each of the stent sections 10 are attached to the rod 14 by a base member 18.

Figure 4:
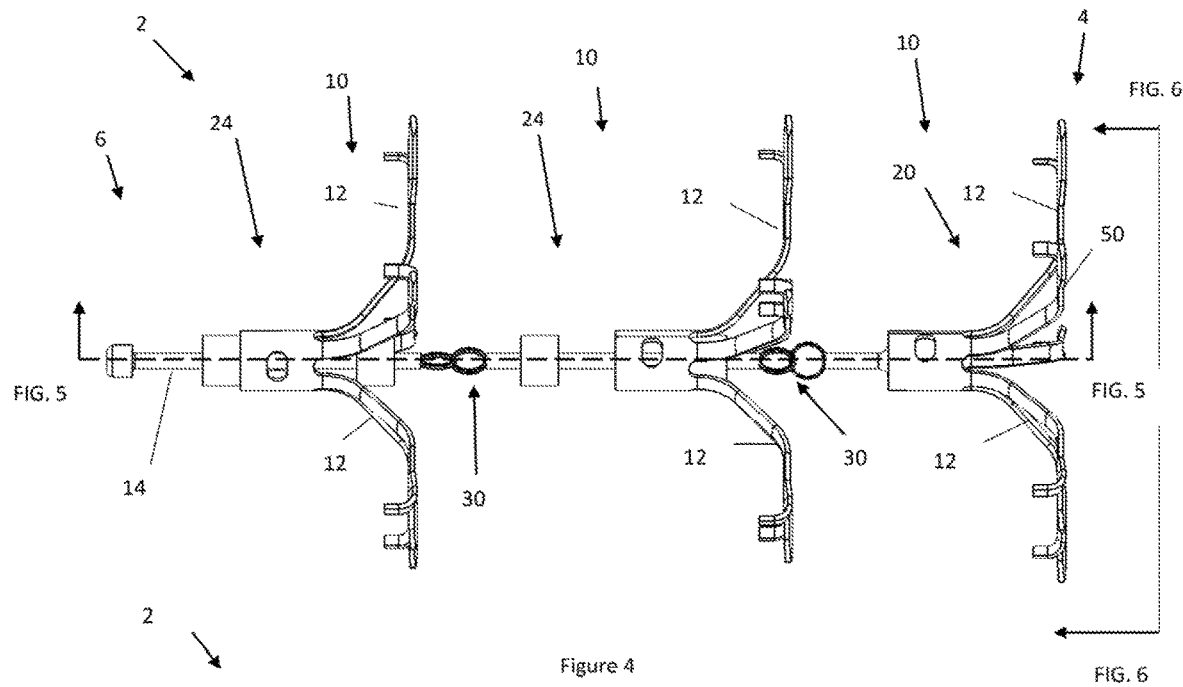
FIG. 4 illustrates an elevational view of a plurality of stent sections connected together by a hinge point.

FIG. 4 illustrates a plurality of stent sections 10 and rods 14 connected together at a hinge point 30 forming a stent 2 that has a distal end 4 and a proximal end 6 with a longitudinal axis 50 extending there-between. Each of the stent sections 10 are connected to a rod 14 that assists in insertion and/or removal of the stent 2 into or out of a region of interest. The stent section 10 at the distal end 4 includes a fixed anchor 20 so that when the struts 12 are connected to a wall of a passageway (not shown) the stent sections 12 at the distal end are free of movement along the rod 14. Each of the stent sections 10 include a movable anchor 24 that is located on the proximal side 6 of the base member 18 of each stent section 10 on the distal end 4 that prevents the stent sections 10 from being removed from the rod 14 but allows each of the stent sections 10 to move along their respective section of rod 14 as the struts 12 expand and work to expand a passage (not shown). The hinge points 30 assist in allowing the stent 2 to move through a tortuous passageway as well as the hinge points 30 may be releasable so that one or more of the stent sections 10 and corresponding struts 12 may be removed while the remaining stent sections 10 are retained within a passageway (not shown).

Figure 5:
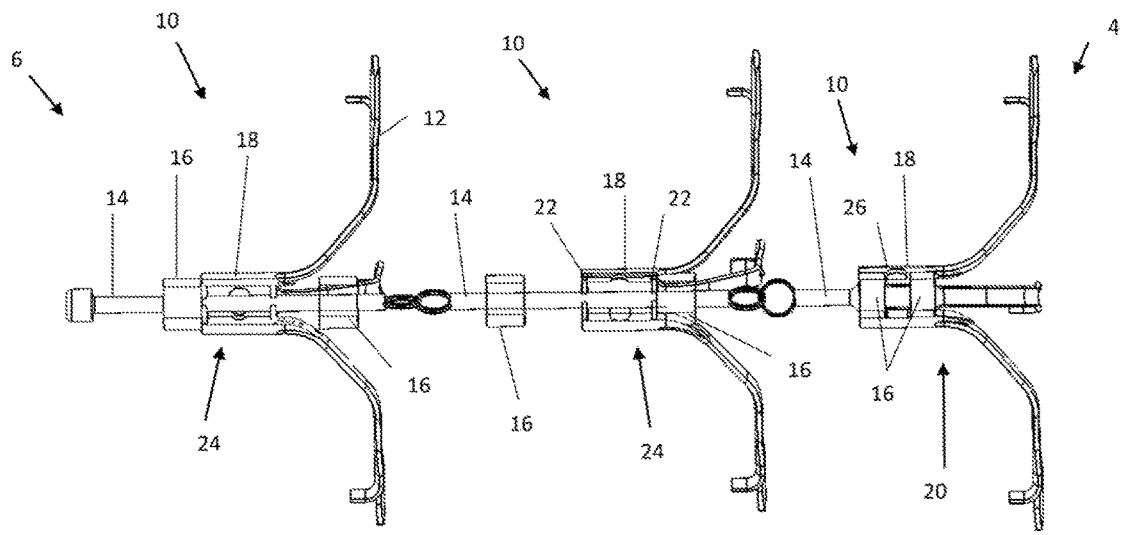
FIG. 5 illustrates a cross-sectional view of the stent of FIG. 4.

FIG. 5 illustrates a cross-sectional view of the stent 2 of FIG. 4. The stent 2 as shown has three stent sections 10. Two stent sections 10 which are located towards the proximal end 4 have movable anchors 24, and one stent section 10 located at the distal end 6 has a fixed anchor 20. The movable anchors 24 include a rod 14 extending therethrough with stops 16 connected to the rod 14 that are located on either side of the base member 18 of the movable anchors 24 so that the movable anchor 24 can move between the stops. Each end of the movable anchors 24 include a movable anchor stop 26 that contacts the stops 16 and limits axial movement but allows for some axial movement and expansion of the struts 12. The fixed anchor 22 includes a movable anchor stop 26 that extends between two closely located stops 16 so that all movement of the fixed anchor 22 is prevented.

Figure 6:
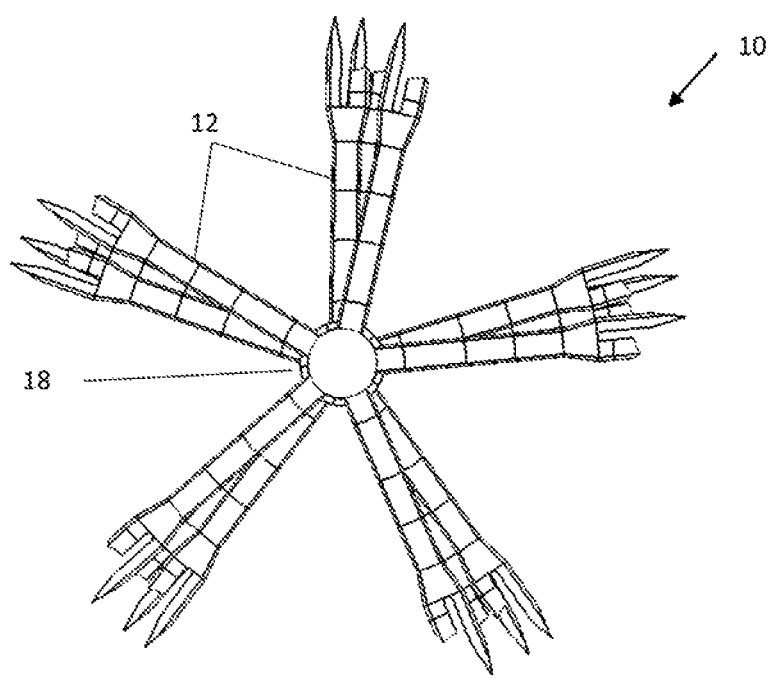
FIG. 6 illustrates an end view of the stent of FIG. 4.

FIG. 6 illustrates an end view of the stent 2 and the stent sections 10 of FIG. 4. A plurality of struts 12 are shown extending radially outward from a base member 18. A rod (not shown) extends through the base member 18. The struts 12 extend from the rod (not shown) to open a passage (not shown).

Figure 7:
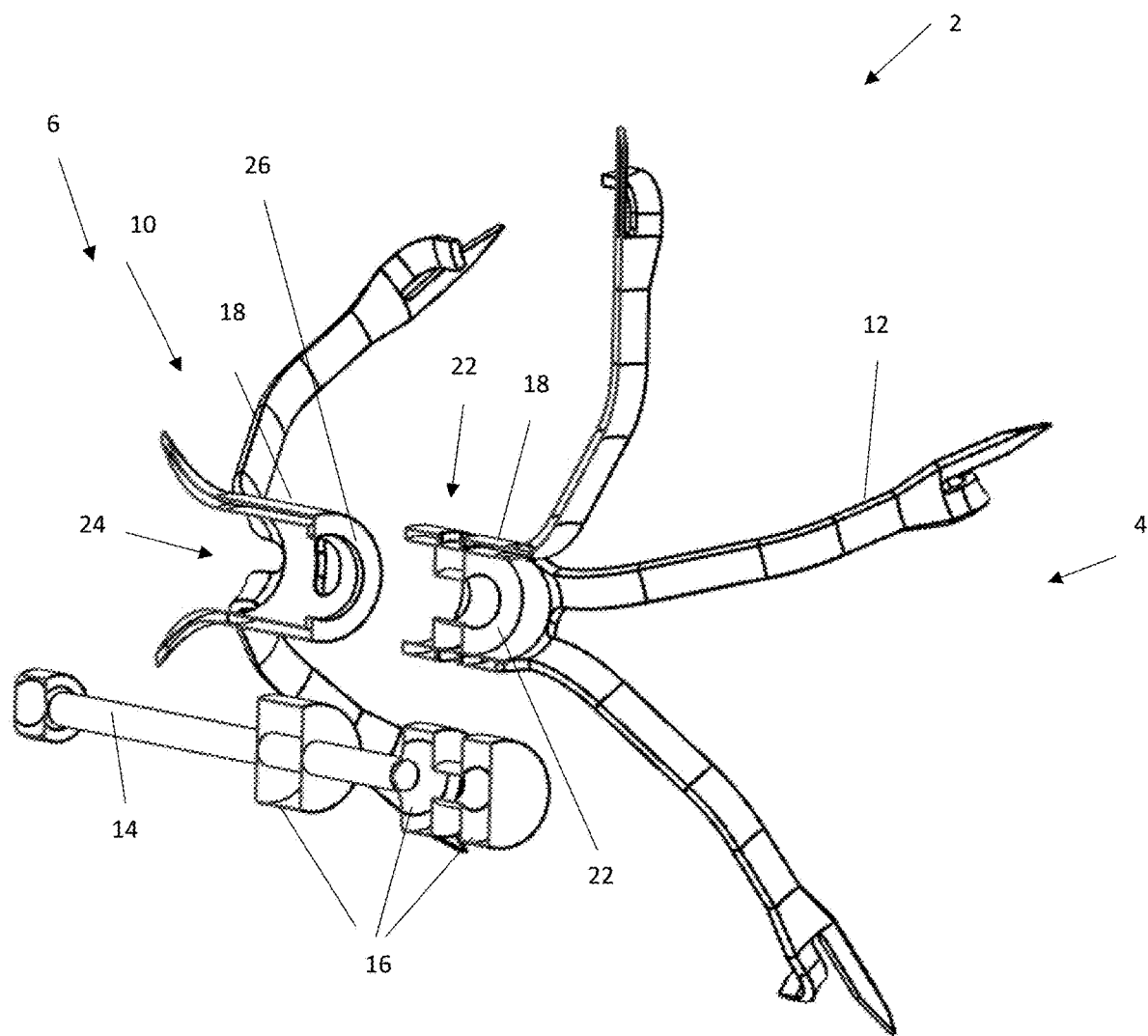
FIG. 7 is an exploded view of the stent of FIG. 1.
Figure 8:
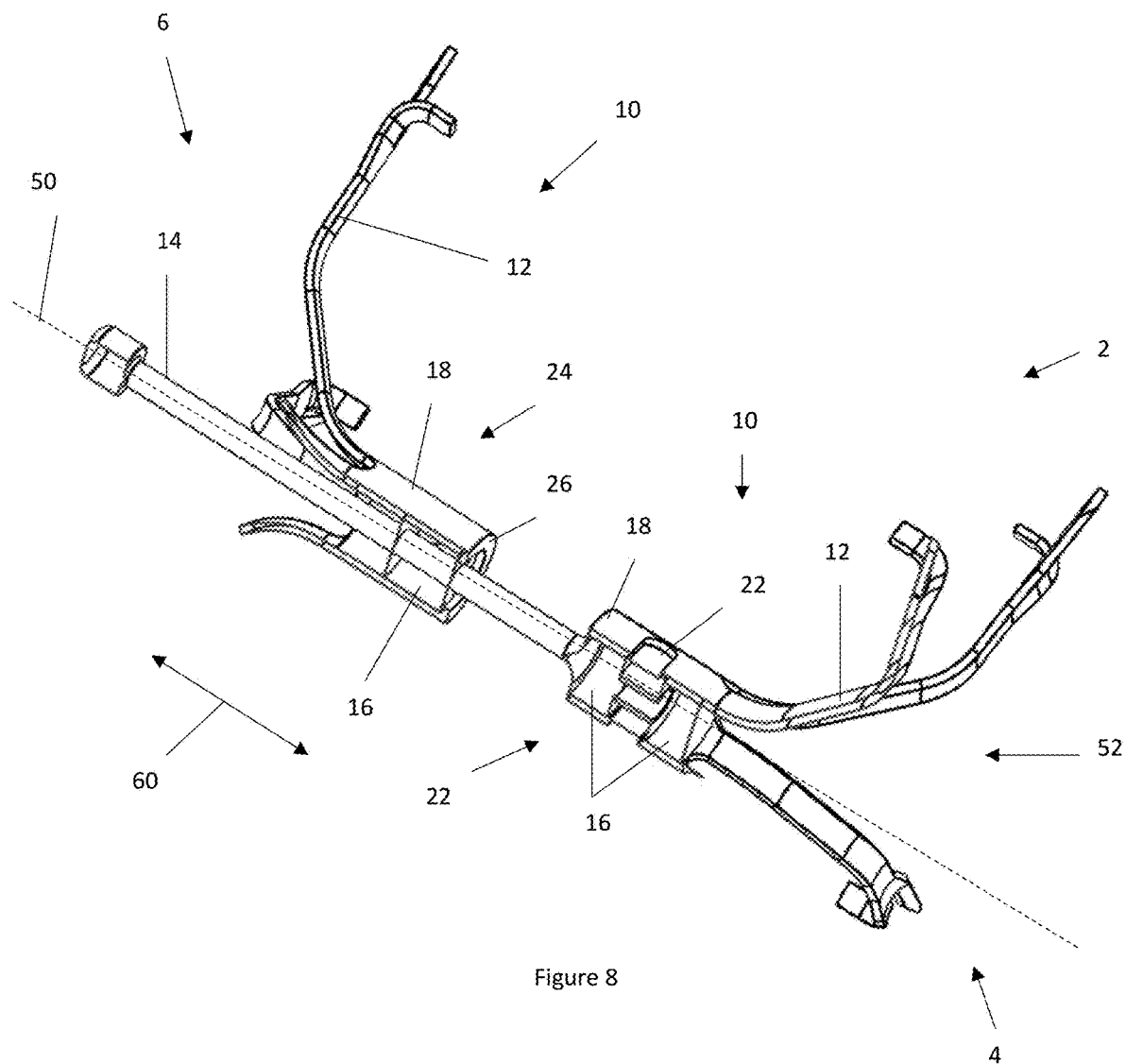
FIG. 8 is a perspective view of the stent of FIG. 1.

FIG. 7 is an exploded view of the stent 2 of FIG. 1, the stent 2 having a distal end 4 and a proximal end 6. The stent 2 has a plurality of stent sections 10 connected to a rod 14 that extends fully and/or partially through each of the pair of stent sections 10. Each of the stent sections 10 include a base member 18 that supports a plurality of struts 12. The rod 14 includes a pair of stops 16 with one stop 16 being located in a distal end region at the distal end 4 and one stop 16 being located between the distal end 4 and the proximal end 6. Each of the stent sections 10 includes a base member 18 with a plurality of struts 12 extending therefrom and one or more anchors (20, 24). The stent sections 10 include struts 12 that are movable from a retracted state (not shown) to a deployed state (as shown). As shown, one base member 18 includes a fixed anchor 20 and one base member 18 includes a movable anchor 24. The fixed anchor 20 is located at a distal end 4 of the rod 14 and includes a connection stop 22 that is in communication with stop 16 so that movement of the rod 14 with respect to base member 18 is prevented at the distal end 4. The base member 18 towards the proximal end 6 includes a movable anchor 24 so that the movable anchor 24 is moved towards or away from the distal end 4 and proximal end 6. The movable anchor 24 includes a movable anchor stop 26 that maintains the movable anchor 24 in communication with the stop 16 and prevents the stent section 10 from being moved. FIG. 8 is a perspective view of the stent of FIG. 1, with the stent 2 having a distal end 4 and a proximal end 6. The stent 2 has a plurality of stent sections 10 connected to a rod 14 that extends fully and/or partially through each of the pair of stent sections 10. Each of the stent sections 10 include a base member 18 that supports a plurality of struts 12. The rod 14 includes a pair of stops 16 with one stop 16 being located in a distal end region at the distal end 4 and one stop 16 being located between the distal end 4 and the proximal end 6. Each of the stent sections 10 includes a base member 18 with a plurality of struts 12 extending therefrom and one or more anchors (20, 24). The stent sections 10 include struts 12 that are movable from a retracted state (not shown) to a deployed state 52. As shown, one base member 18 includes a fixed anchor 20 and one base member 18 includes a movable anchor 24. The fixed anchor 20 is located at a distal end 4 of the rod 14 and includes a connection stop 22 that is in communication with stop 16 so that movement of the rod 14 with respect to base member 18 is prevented at the distal end 4. The base member 18 towards the proximal end 6 includes a movable anchor 24 so that the movable anchor 24 is moved along the longitudinal axis 50 in the direction 60 towards or away from the distal end 4 and proximal end 6. The movable anchor 24 includes a movable anchor stop 26 that maintains the movable anchor 24 in communication with the stop 16 and prevents the stent section 10 from being moved.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Stent
4 Distal end
6 Proximal end
10 Stent Section
12 Strut
13 Tang
14 Rod
16 Stop
18 Base member
20 Fixed Anchor
22 Connection stop
24 Movable anchor
26 Movable anchor stop
30 Hinge point
32 Interconnect
50 Longitudinal axis
52 Deployed state
54 Retraction state
60 Direction

We claim:

1. A stent comprising:
two or more stent sections;
a plurality of struts connected to each of the two or more stent sections,
one or more rods extending between the two or more stent sections;
wherein a first of the two or more stent sections are fixedly connected to one of
the one or more rods by a fixed anchor that prevents longitudinal movement of the first of the two or more stent sections relative to the one or more rods, and a second of the two or more of stent sections are movably connected to one of the one or more rods by a movable anchor;
wherein the plurality of struts extend outward away from the one or more rods to support an opening of an anatomical passageway so that airflow through the anatomical passageway is increased by the support and the opening of the anatomical passageway by the stent;
wherein the movable anchor allows the second of the two or more stent sections to longitudinally slide along a longitudinal axis of the stent with respect to the first of the two or more stent struts as the plurality of struts expand outward from a retracted state to a deployed state; and
wherein the stent has a distal end and a proximal end and the plurality of the struts of the first of the two or more stent sections are located at the distal end and the plurality of struts of the second of the two or more stent sections are located at the proximal end and the fixed anchor and the movable anchor are located between plurality of the struts at the distal end and the plurality of the struts at the proximal end.

2. The stent of claim 1, wherein the first of the two or more stent sections is connected to a first rod of the one or more rods and the second of the two or more stent sections is connected to a second rod of the one or more rods and a hinge point is located between the first rod and the second rod so that the first of the two or more stent sections and the first rod are spaced apart from the second of the two or more stent sections and the second rod by the hinge point.

3. The stent of claim 2, wherein the hinge point includes an interconnect connected to a distal end of the first rod and an interconnect connected to a proximal end of the second rod and the interconnect of the first rod and the interconnect of the second rod are connected together.

4. The stent of claim 1, wherein the stent is compacted into a cartridge, a catheter, or both prior to insertion.

5. The stent of claim 1, wherein the stent includes a removal rod.

6. The stent of claim 1, wherein the one or more rods include a stop for each of the two or more stent sections so that each of the two or more stent sections are retained on the one or more rods.

7. The stent of claim 6, wherein the movable anchor moves about one of the stops and the stop prevents the movable anchor from being removed from one of the one or more rods, and the fixed anchor is fixedly connected to one of the stops.

8. The stent of claim 7, wherein the movable anchor includes a distal end and a proximal end and the distal end, the proximal end, or both include one or more movable stops that contact the stop of the rod and prevent the movable anchor from being removed from the rod.

9. The stent of claim 1, wherein each of the struts includes about three or more turns so that the struts form an angle of about 85 degrees or more.

10. The stent of claim 1, wherein the anatomical passageway is an air way and the air way is a second division or a third division of an air way.

11. The stent of claim 1, wherein the stent is made from nitinol.

12. The stent of claim 1, wherein the fixed anchor of the first of the two or more stent sections includes a connection stop that extends between a pair of stops of the one or more rods so that the connection stop and the pair of stops prevent longitudinal movement of the first of the two or more stent sections relative to the one or more rods.

13. The stent of claim 1, wherein the connection stop is a weld, crimp, friction fitting, shrinking, an interlock, a chemical connection, or a combination thereof.

14. The stent of claim 1, wherein the stent gradually opens the anatomical passageway and maintains openness of the anatomical passageway.

15. The stent of claim 1, wherein the two or more stent sections include a third stent section.

16. The stent of claim 15, wherein the first stent section is connected to a first rod of the one or more rods, the second stent section is connected to a second rod of the one or more rods, and the third stent section is connected to third rod of the one or more rods.

17. The stent of claim 16, wherein the first rod and the second rod are connected by one or more hinge points, the second rod and the third rod are connected by one or more hinge points and wherein the one or more hinge points are one or more interconnects that are interlocking loops that permit the first rod and the second rod to move relative to each other and the second rod and the third rod to move relative to each other.

18. A method comprising:

a. loading the stent of claim 1 into a cartridge;

b. inserting the cartridge into a deployment apparatus; and c. deploying the stent into a location of interest.

19. The method of claim 18, wherein the stent elastically deforms from the retracted state to the deployed state after the stent has been deployed.

\* \* \* \* \*